United States Patent [19]

Milberger et al.

[11] Patent Number: 4,599,430
[45] Date of Patent: Jul. 8, 1986

[54] NITROGENATION OF HYDROCARBONS, INCLUDING THE PRODUCTION OF MALEIMIDE

[75] Inventors: Ernest C. Milberger, Solon; Eunice K. T. Wong, Cleveland, both of Ohio

[73] Assignee: The Standard Oil Company, Cleveland, Ohio

[21] Appl. No.: 576,294

[22] Filed: Feb. 2, 1984

Related U.S. Application Data

[63] Continuation of Ser. No. 332,623, Dec. 21, 1981, abandoned.

[51] Int. Cl.$^4$ ............................................. C07D 207/24
[52] U.S. Cl. .................................... 548/548; 548/549; 549/258; 558/323; 558/325
[58] Field of Search ...................... 260/465.3; 548/548

[56] References Cited

U.S. PATENT DOCUMENTS

| | | | |
|---|---|---|---|
| 3,126,407 | 3/1964 | Cottle et al. | 260/465.3 |
| 3,161,670 | 12/1964 | Adams et al. | 260/465.3 |
| 3,342,849 | 9/1967 | Brill et al. | 260/465.3 |
| 3,345,397 | 10/1967 | Finley | 260/465.3 |
| 3,397,210 | 8/1968 | Michalowicz | 260/326.5 |
| 3,412,134 | 11/1968 | Jones | 260/465.3 |
| 3,721,724 | 3/1973 | Uebele et al. | 525/282 |
| 3,819,679 | 6/1974 | Sheely | 260/465.3 |
| 3,859,326 | 1/1975 | Saito et al. | 260/465.3 |
| 3,899,509 | 8/1975 | Riemenschneider | 260/326.5 FM |
| 3,904,653 | 9/1975 | Milberger et al. | 252/470 X |
| 3,907,834 | 9/1975 | Milberger et al. | 252/456 X |
| 3,944,592 | 3/1976 | Sheely | 260/465.3 |
| 3,960,887 | 6/1976 | Renard | 260/326.5 FM |
| 4,018,712 | 4/1977 | Li | 260/465.3 X |
| 4,070,393 | 1/1978 | Angstadt | 260/464 X |
| 4,155,920 | 5/1979 | Milberger et al. | 549/258 |
| 4,240,931 | 12/1980 | Milberger et al. | 252/438 |
| 4,246,191 | 1/1981 | Pujado | 260/465.3 |
| 4,436,671 | 3/1984 | Furuoya et al. | 260/465.3 |

FOREIGN PATENT DOCUMENTS

| | | | |
|---|---|---|---|
| 2244264 | 3/1973 | Fed. Rep. of Germany | 260/465.3 |
| 1394207 | 5/1975 | United Kingdom | 260/465.3 |

OTHER PUBLICATIONS

Alfa Catalog, 1983; Morton Thiokol, Inc., (Alfa Products), pp. 362–363.
Aldrich Catalog/Handbook of Fine Chemicals; Aldrich Chemical Co., 1984; (2 unnumbered pages).

*Primary Examiner*—Joseph Paul Brust
*Attorney, Agent, or Firm*—Thomas P. Schur; Joseph G. Curatolo; Larry W. Evans

[57] ABSTRACT

A process is provided for the nitrogenation of hydrocarbons, resulting in the production of cyclic imides and nitriles from hydrocarbons contacted with molecular oxygen and a nitrogenating agent, including ammonia or primary amines, in the presence of an oxidation catalyst containing variable valency metal oxides, in the vapor phase at elevated temperature.

14 Claims, No Drawings

NITROGENATION OF HYDROCARBONS, INCLUDING THE PRODUCTION OF MALEIMIDE

This is a continuation of application Ser. No. 332,623 filed Dec. 21, 1981, now abandoned.

BACKGROUND OF THE INVENTION

The present invention is directed to the nitrogenation of hydrocarbons, preferably of unsaturated hydrocarbons.

More particularly, the process of the present invention is directed to the nitrogenation of hydrocarbons in order to produce cyclic imides and dinitriles. Preferably, unsaturated hydrocarbons having from 4 to about 9 carbon atoms are catalytically nitrogenated in the presence of oxygen at an elevated temperature to produce cyclic imides such as N-substituted and unsubstituted maleimide and dinitriles such as fumaronitrile and maleonitrile. The source of nitrogen is ammonia, or in the case of N-substituted maleimide production, a primary amine.

Cyclic imides such as maleimide are produced by several methods. U.S. Pat. No. 3,960,887 to Renard discloses the production of N-substituted maleimides by reacting maleic anhydride and a primary amine in a solvent for the anhydride and amine under a pressure of from 1 to 5 bars and at a temperature of from 40° C. to 130° C.

U.S. Pat. No. 3,397,210 to Michalowicz discloses a process for producing maleimide or a substituted maleimide by reacting in the vapor phase, ammonia or a primary amine which maleic anhydride in the presence of an acidic alumina containing catalyst.

U.S. Pat. No. 3,899,509 to Riemenschneider discloses a continuous, recycle type process for the manufacture of maleic acid imide from pure or hydrocarbon-mixed maleic anhydride and ammonia by reacting the components in the gaseous phase, in the presence of a dehydration catalyst (alumina). These prior art methods are complex, and costly.

Cyclic imides such as maleimide are useful as monomers and comonomers in the production of high impact strength copolymers. U.S. Pat. No. 3,721,724 to Uebele et al. and assigned to our common assignee herein discusses the marked improvement in ASTM heat distortion temperatures exhibited by copolymers containing acrylonitrile, styrene and butadiene when substituted or unsubstituted maleimide was incorporated in the copolymer. N-substituted maleimides have been used as antibacterial and antifungal agents.

Dinitriles are conventionally produced by reacting dichloro-substituted hydrocarbons with NaCN, or by dimerizing unsaturated mononitriles of one-half the desired carbon number. Dinitriles are useful as comonomers for the production of polymers, and dinitriles are also hydrogenated to form diamines which are used as monomers in polyamide polymers.

The preparation of dinitriles as generally commercially practiced requires the use of corrosive halides and NaCN, while the preparation of cyclic imides such as maleimide is not practiced on a wide scale, due to the complexity of the known preparation processes, low yields of product obtained, and relatively high cost of raw material feedstock.

U.S. Pat. No. 4,070,393 describes the ammoxidation of alkyl-substituted hydrocarbons to produce nitriles and dinitriles utilizing conventional ammoxidation catalysts.

SUMMARY OF THE INVENTION

It is therefore an object of the present invention to provide a process for producing cyclic imides such as the maleimides in good yields, utilizing relatively inexpensive feedstocks.

It is a further object of the present invention to provide a process for producing dinitriles, avoiding the use of halides such as chlorine and NaCN.

We have found that cyclic imides and dinitriles can be produced in the vapor phase in good yields by the nitrogenation of hydrocarbons, according to the processes of the present invention.

In general, the present invention includes a process for the nitrogenation of hydrocarbons by contacting the hydrocarbon with ammonia or a primary amine and molecular oxygen or an oxygen-containing gas in the vapor phase at elevated temperature in the presence of an oxidation catalyst comprising variable valency-metal oxides.

The present invention therefore provides a process for the production of cyclic imides by contacting hydrocarbons having at least 4 carbon atoms with ammonia or a primary amine and molecular oxygen or an oxygen-containing gas in the vapor phase at elevated temperature in the presence of an oxidation catalyst comprising variable valency-metal oxides, and recovering the cyclic imide product.

The present invention additionally provides a process for the production of dinitriles by contacting hydrocarbons with ammonia and molecular oxygen or an oxygen-containing gas in the vapor phase at elevated temperature in the presence of an oxidation catalyst comprising variable valency-metal oxides, including promoted antimony molybdates.

In one embodiment of the invention, a process is provided for the production of maleimide and N-substituted maleimides by contacting an unsaturated hydrocarbon having from 4 to about 9 carbon atoms with ammonia or a primary amine and molecular oxygen or an oxygen containing gas in the vapor phase at an elevated temperature in the presence of an oxidation catalyst comprising at least one variable valency metal oxide, and recovering the maleimide or N-substituted maleimides.

In another embodiment of the invention, a process is provided for the production of fumaronitrile and maleonitrile by contacting butadiene with ammonia and molecular oxygen or an oxygen containing gas in the vapor phase at an elevated temperature in the presence of a catalyst comprising the mixed oxides of antimony and molybdenum.

DETAILED DESCRIPTION OF THE INVENTION

According to the process of the present invention, hydrocarbons which may be nitrogenated include saturated and unsaturated hydrocarbons, such as alkanes, alkenes, alkadienes, aryls and alkyl substituted aryls. For the preparation of cyclic amides particularly, the use of hydrocarbons having 4 to about 9 carbon atoms is preferred, and the use of hydrocarbons having 4 to 5 carbon atoms is most preferred. Also for the preparation of cyclic imides, oxygenated hydrocarbons may also be utilized but are not preferred.

Suitable hydrocarbons include but are not limited to butane, 1-butene, 3-butene, 1,3-butadiene, 1-hexene, isoprene, benzene, 1,2-dimethylbenzene and the like. Suitable oxygenated hydrocarbons include but are not limited to crotonaldehyde, furan, phenol and the like.

The nitrogenating agent in the process of the present invention is preferably ammonia, and for the production of N-substituted cyclic imides, the nitrogenating agents are primary amines. Suitable primary amines include but are not limited to alkyl amines such as methyl, ethyl, propyl and butyl; aryl amines such as phenyl; and, cycloalkyl amines such as cyclohexyl. By "nitrogenation" according to the process of the present invention is meant the addition of at least one nitrogen atom to a hydrocarbon, such that the nitrogen atom added is bonded to at least one carbon atom. The nitrogenation may result in the formation of a nitrile (dinitrile) or an imide.

In the nitrogenation process of the present invention, oxygen is also contacted with the hydrocarbon and nitrogenating agent. It is thought that oxygen acts as a scavenger for excess or available hydrogen resulting from the reaction. In the production of imides, oxygen is actually incorporated into the product molecule. The molecular oxygen is most conveniently added as air, but synthetic streams containing molecular oxygen are also suitable.

In addition to the hydrocarbon, nitrogenating agent and oxygen, other gases may be added to the reactant feed. For example, steam, nitrogen or argon could be added to the reactants as well as recycled $CO_2$ and the like.

The ratio of the reactants may vary. The molar ratio of nitrogenating agent to hydrocarbon may range from at least about 0.5:1 to an excess of nitrogenating agent. For example, a molar ratio of nitrogenating agent to hydrocarbon of about 0.5:1 to about 2:1 generally favors the production of the cyclic imides, with about 0.75:1 to about 1.75:1 being preferred. The molar ratio of nitrogenating agent to hydrocarbon of about 1.75:1 or greater generally favors the production of dinitriles. The molar ratio of oxygen to hydrocarbon is preferably at least about 2:1 to about 30:1. When air is introduced to provide molecular oxygen for the reaction, the ratio of air to hydrocarbon is preferably 8:1 to about 60:1.

The nitrogenation reaction may be conducted at atmospheric, superatmospheric or subatmospheric pressure. The reaction temperature of the vapor phase nitrogenation reaction may vary widely, and is dependent in part upon the particular hydrocarbon and oxidation catalyst utilized. Temperatures of about 250° C. to about 600° C. are utilized, with temperatures of about 375° C. to about 475° C. being preferred.

The nitrogenation process of the present invention occurs when the hydrocarbon, nitrogenating agent and oxygen are contacted in the vapor phase at elevated temperatures in the presence of an oxidation catalyst. By oxidation catalyst is meant a catalyst suitable for the oxidation of hydrocarbons, the catalyst comprising variable valency metal oxides. Such variable valency metal oxides include molybdenum, antimony, titanium, zirconium, hafnium, vanadium, niobium, tantalum, chromium, tungsten, manganese, iron, cobalt, nickel, copper, ruthenium and the platinum metals including platinum, palladium, rhodium and iridium. According to the process of the present invention, the use of oxidation catalysts containing molybdenum and/or antimony are preferred.

The oxidation catalyst utilized may be promoted with variable valency metal oxides, or other suitable oxidation catalyst promoter elements. Consequently, the oxidation catalyst utilized in the process of the present invention may include (without being limited to) promoter elements such titanium, zirconium, niobium, tantalum, vanadium, iron, aluminum, zinc, cadmium, platinum, ruthenium, boron, germanium, tin, phosphorus, arsenic, bismuth, tellurium, silver, rare earths such as cerium, thallium, thorium, uranium, the alkali metals and alkaline earths, particularly magnesium.

Suitable oxidation catalysts for the process of the present invention include the antimony molybdates, vanadyl molybdates, phosphomolybdates, bismuth molybdates, iron antimonates, molybdenum tungstates, vanadium phosphates, and the like.

While molybdenum oxide alone catalyzes the nitrogenation process of the present invention, more preferred catalysts include antimony molybdates, such as are disclosed in U.S. Pat. No. 3,907,834. These catalysts are represented by the formula $$A_aMo_bSb_cO_x$$

wherein A is a metal or oxide selected from the group consisting of molybdenum, tungsten, magnesium, aluminum and nickel, and a is a number from 0 to about 0.2, preferably about 0.001 to about 0.2, b is a number of from about 1 to about 9, preferably about 1 to about 8, c is a number from 1 to 9, preferably 1 to about 8 and x is a number determined by the valence requirements of the combined elements, preferably, wherein at least some of the molybdenum in the catalyst is at a valence state below +6.

Other preferred catalysts include antimony molybdates such as are disclosed in U.S. Pat. No. 3,904,653, represented by the formula $$A_aMo_bSb_cV_dFe_eO_x$$

wherein A is a metal or an oxide selected from molybdenum, tungsten, magnesium, aluminum and nickel and wherein
- b and c are numbers from about 1 to about 9, preferably about 1 to about 8,
- a, d and e are numbers from 0 to about 1,
- d and e preferably about 0.01 to about 0.5,
- d+e is not zero, and
- x is a number which satisfies the valence requirements of the other elements present.

Also preferred are antimony molybdate catalysts such as are disclosed in U.S. Pat. No. 4,240,931, and which are represented by the formula $$A_aMo_bSb_cD_fE_gO_x$$

wherein
- A is a member selected from the group consisting of a finely divided metal or oxide of molydenum, tungsten, magnesium, aluminum, or nickel;
- D is at least one element selected from the group consisting of niobium, zirconium, titanium and tantalum;
- E is selected from the group consisting of lithium, silver, cerium, cadmium, cobalt, arsenic, zinc, germanium, bismuth, ruthenium, platinum and uranium; and wherein
- a is a number from 0 to about 0.2; preferably about 0.001 to about 0.2,
- b and c are numbers from 1 to 9; preferably about 1 to about 8,
- f is a number from about 0.01 to about 6, preferably about 0.01 to about 3,
- g is a number from 0 to 1; preferably about 0.01 to about 0.5,
- x is a number which satisfies the valence requirements of the other elements present; and
- wherein at least some of the molybdenum in the catalyst is maintained at a valence state below +6.

The oxidation catalysts suitable for the process of the present invention may be prepared by methods well known in the art, including those methods described in the above mentioned patents. Generally, the oxidation catalysts may be prepared by mixing compounds containing the catalyst components in a liquid such as water, preferably with heating, recovering a catalyst precursor such as by filtration or evaporation, drying and calcining the precursor, preferably in the presence of oxygen, at elevated temperature. Suitable component containing compounds include oxides, hydroxides and salts of the catalyst component elements such as nitrates, halides, carbonates, acetates, formates, and the like.

The catalysts may be used alone or a support could be employed. Suitable supports include alumina, alumina-silica, silica, silicon carbide, titania, zirconia and the like. The catalysts may be used in a fixed-bed reactor using tablets, pellets or the like or in a fluid bed reactor using catalysts preferably having a particle size of less than about 300 microns.

The contact time may be a as low as a fraction of a second or as high as about 40 seconds. For fixed bed operations, however, a contact time of about 0.1 to about 10 seconds is preferred, with 1 to 5 seconds being most preferred. Generally, selectivity to cyclic imides increases as contact time is increased.

The products of the present invention, particularly cyclic imides are generally recovered from the reactor effluent by passing the effluent stream through a scrubber solution containing an acidified solvent. The solvent could comprise an aqueous solution of a mineral acid, the solution having a pH of less than 7. The acidified solution scavanges excess $NH_3$, and prevents hydrolysis of the cyclic imide product. Suitable organic solvents may also be utilized.

SPECIFIC EMBODIMENTS OF THE INVENTION

The oxidation catalysts tested for activity in the nitrogenation process of the present invention were run according to the following procedure, except where otherwise noted.

A 20 cc downflow fixed bed reactor consisting of a length of stainless steel tubing having an outer diameter of about 1.3 cm and having a ful length 0.31 cm axial thermowell was charged with 20 cc catalyst. The reactor was heated with a split stainless steel block furnace. Liquid and gaseous reactor effluents were collected and were analyzed by gas chromatography. Identification of the major products was confirmed by NMR and/or IR analysis.

The reaction conditions for the catalyst test runs are reported in the Tables below, including temperature, feed ratios and contact time. All tests were run at atmospheric pressure. Test results reported in the Tables are stated in terms as follows.

$$\text{Single Pass Yield} = \frac{\text{Mole of Product Formed} \times 100}{\text{Moles of Hydrocarbon Fed}}$$

$$\text{Total Conversion} = \frac{\text{Moles of Hydrocarbon Reacted} \times 100}{\text{Moles of Hydrocarbon Fed}}$$

Abbreviations used in the Tables have the meanings as follows:
- AN: Acrylonitrile
- FN: Fumaronitrile
- HC: Hydrocarbon
- MAH: Maleic Anhydride
- MI: Maleimide
- MN: Maleonitrile

EXAMPLES 1-2

Catalysts of the formula $MoO_x + Mo°_{0.05}$ were prepared by mixing 95.96 g $MoO_3$ and 0.96 g molybdenum metal in one liter water with refluxing for 3.5 hours. The slurry was evaporated to a paste with heating, and was thereafter heated to dryness at about 150° C. The catalyst was ground and screened to 10–30 mesh (0.595–2.0 cm) and 20 cc were charged to the reactor for testing according to the above procedure.

In the above catalyst formula, x is the number needed to satisfy the valence requirements of the other element. The addition of metallic molybdenum indicates that the valence of the molybdenum oxide present has been reduced below the +6 state, in this case, by the addition of the molybdenum metal. It is assumed that the metal so added, in reducing the molybdenum oxide present, has itself been oxidized to a higher, yet undetermined valency. A more detailed description of the valence reduction of molybdenum in catalyst prepration is contained in U.S. Pat. No. 3,904,653.

As is demonstrated by the results reported in Table I for the nitrogenation of 1,3 butadiene, the variable valency metal oxide, molybdenum oxide itself is an effective catalyst for the process of the present invention.

EXAMPLES 3-9

Catalysts of the formula $SbMo_3O_x+Mo°_{0.06}$ were prepared by mixing 72 g $MoO_3$ and 0.96 g molybdenum metal in water with heating at reflux for about 2.5 hours. To the slurry was added 24.27 g $Sb_2O_3$, followed by heating at reflux conditions for an additional hour. The slurry was then evaporated with heating to a paste, which was dried at about 130° C. for about 16 hours. The catalysts were screened to 10-30 mesh, and were charged to the reactor for testing. Test results are reported in Table I.

As is demonstrated in Table I, in the butadiene nitrogenation reaction, according to the process of the present invention, the major nitrogenated products are the cyclic imide, maleimide, and the unsaturated dinitrile mix of fumaronitrile and maleonitrile. A competing reaction, of oxygen and butadiene, produces maleic anhydride as a byproduct. Acrylonitrile is also produced as a byproduct, presumably when cleavage of a carbon atom from a butadiene molecule results in a propylene-like intermediate being available for conventional ammoxidation. The nitrogenation reaction of the present invention does not, however proceed by the conventional ammoxidation reaction mechanism. For example, in the nitrogenation of 1,3-butadiene, there are no allylic hydrogens present in the molecule for easy abstraction and replacement as in the ammoxidation process. The nitrogenation mechanism of the present invention is not clear, but because of the absence of allylic hydrogen, is readily distinguishable from conventional ammoxidation.

Carbon atom cleavage also accounts for the appearance of the minor byproducts of the nitrogenation process. Included are oxidation byproducts such as acrylic acid and acrolein, the waste carbon monoxide and carbon dioxide, and nitrogenation byproducts such as acetonitrile and HCN.

EXAMPLES 10-19

Antimony molybdate oxidation catalysts having varying Sb/Mo ratios were prepared by adding the amounts of molybdenum oxide listed below to 0.96 g molybdenum metal in 1 liter water, heating with stirring to reflux for 2.5 hours, and adding the amounts of $Sb_2O_3$ listed below to the mixture. Catalyst preparation and testing then continued by the procedure of Examples 3-9.

TABLE IIa

| Example Nos. | Grams Mo Added | Grams Sb Added | Catalyst |
|---|---|---|---|
| 10-11 | 63.97 | 32.39 | $SbMo_2O_x + Mo°_{0.06}$ |
| 12-13 | 68.54 | 27.76 | $SbMo_{2.5}O_x + Mo°_{0.06}$ |
| 14-15 | 72.00 | 24.27 | $SbMo_3O_x + Mo°_{0.06}$ |
| 16-17 | 74.64 | 21.59 | $SbMo_{3.5}O_x + Mo°_{0.06}$ |
| 18-19 | 76.77 | 19.43 | $SbMo_4O_x + Mo°_{0.06}$ |

Test results are reported in Table IIb. The antimony molybdate catalysts exhibit effective activity for the nitrogenation process of the present invention over ranges of Sb/Mo ratios.

EXAMPLES 20-31

Catalysts having the formula $SbMo_3Ti_{0.6}Nb_{0.1}O_x+Mo°_{0.06}$ were prepared by the procedure of Examples 3-9 and were tested for the nitrogenation of 1,3-butadiene, as reported in Table III, and while varying the ratio of $NH_3$ to hydrocarbon. These test results are reported in Table IV, demonstrating that $NH_3$/hydrocarbon ratios of about 0.5 to between 1.5 and 2 favor production of maleimide, while dinitrile production begins to increase at a $NH_3$/hydrocarbon ratio of 1 and is most favored when the ratio reaches 2 or greater. The absence of nitrogenating agent results in the production of the byproduct maleic anhydride, which is itself a major product of this particular reaction/catalyst system when $NH_3$/hydrocarbon ratios are low.

EXAMPLES 38-42

Catalysts of the formula $SbMo_3Ti_{0.6}Nb_{0.1}O_xMo°_{0.06}$ were prepared according to the procedure of Examples 3-9 and were tested for butadiene nitrogenation while varying contact time. Test results reported in Table V indicate that increased contact time favors production of maleimide.

TABLE I

Nitrogenation of 1,3-Butadiene

| Example No. | Temp. °C. Bath/Bed | HC/NH$_3$/Air Ratio | Contact Time (Sec) | % Molar Yield ||||| 
|---|---|---|---|---|---|---|---|---|
| | | | | MI | FN | MN | AN | MAH |
| $MoO_x + Mo°_{0.05}$ | | | | | | | | |
| 1 | 409/426 | 1/1.25/44 | 3.6 | 11.6 | 1.9 | | | |
| 2 | 404/413 | 1/1.25/44 | 3.7 | 9.9 | 1.9 | | | |
| $SbMo_3O_x + Mo°_{0.06}$ | | | | | | | | |
| 3 | 390/405 | 1/1.25/44 | 2.1 | 16.0 | 11.3 | 3.7 | 6.1 | 15.3 |
| 4 | 395/411 | 1/1.25/44 | 2.1 | 21.9 | 13.6 | 1.3 | 7.6 | 15.5 |
| 5 | 400/420 | 1/1.25/44 | 2.1 | 20.4 | 11.9 | 3.1 | 5.4 | 20.5 |
| 6 | 409/428 | 1/1.25/44 | 2.1 | 14.4 | 9.8 | 1.3 | 5.8 | 21.5 |
| 7 | 393/416 | 1/1.13/34 | 1.8 | 20.9 | 6.7 | 2.2 | 4.5 | 20.9 |
| 8 | 393/425 | 1/1.54/47 | 1.8 | 29.7 | 13.0 | 0.7 | 7.3 | 15.1 |
| 9 | 388/409 | 1/1.50/45 | 1.8 | 30.2 | 15.1 | 1.9 | 7.8 | 11.8 |

EXAMPLES 47-52

Because maleic anhydride is a byproduct of the nitrogenation reaction of butadiene in which maleimide is produced, teses were devised to determine whether the nitrogenation mechanism included a first step production of maleic anhydride and a second step imidization to produce maleimide, or whether the reaction proceeded in one step to the cyclic imide.

In Example 47, a catalyst of the formula $SbMo_3O_x + Mo°_{0.06}$ was prepared as in Examples 3-9, and was charged to the reactor. The reactor was modified in that the ammonia feed was introduced in the middle of the catalyst bed, while the 1,3-butadiene and oxygen (air) inlet remained at the top of the catalyst bed (in the downflow reactor).

As reported in Table VI, when ammonia was added to the reactor only after the bulk of the butadiene fed was able to react to produce maleic anhydride as in Example 47, no maleimide product was detected. This phenomenon evidences a one step mechanism for the production of cyclic imides in the nitrogenation process of the present invention. It further evidences a mechanism for the prduction of maleimide from butadiene and the like which does not proceed through maleic anhydride as an intermediate. The small yield of dinitrile product detected in the reactor run of Example 47 is attributable to butadiene breakthrough (which had not been converted to maleic anhydride) and reaction of the butadiene by nitrogenation.

In Examples 48-51 $SbMo_3O_x + Mo°_{0.06}$ catalysts prepared as in Examples 3-9 were charged to the modified reactor. In Examples 48-49, ten cc quartz chips were charged to the bottom of the reactor, and ten cc catalyst were charged to the top of the reactor, such that butadiene and air passed first over the catalyst and then together with ammonia over the quartz. In Example 48, no ammonia was added, and only maleic anhydride was produced with no nitrogenation detected. In Example 49, ammonia was added, but again, only maleic anhydride was produced. The production of maleimide, therefore, is not merely an uncatalyzed vapor phase phenomenon involving maleimide and ammonia. Test results for these Examples are reported in Table VI.

In Example 50, the reactor was charged and tested as in Example 49, except that 10 cc alumina having a surface area of about 250 m²/g was substituted for the quartz chips. No maleimide and no maleic anhydride were detected. Trace amounts of acrylonitrile byproduct and fumaronitrile were detected however, suggesting that a portion of the hydrocarbon/$NH_3$/air feed passed over some part of the catalyst. There was substantial coke formation on the alumina, and high CO/$CO_2$ production, accounting for the lack of carbon containing products. In Example 51 the reactor was charged and tested as in Example 49, except that the alumina charged had a surface area of about 75 m²/g. Again there was no maleimide or maleic anhydride detected. Substantial coke formation and high CO/$CO_2$ production was again observed, and small amounts of acrylonitrile and dinitriles were detected. A two step mechanism with a maleic anhydride intermediate for the production of maleimide again was not evidenced. Test results are reported for these Examples in Table VI.

In Example 52, a catalyst prepared as in Examples 47-51 was tested as a check against those Examples. The butadiene, ammonia and air were co-fed over the catalyst bed. Maleimide, fumaronitrile and maleonitrile were produced, according to the nitrogenation process of the present invention, as reported in Table VI.

TABLE IIb

Nitrogenation of 1,3-Butadiene - Varying Sb/Mo Ratio

| Example No. | Catalyst | Temp. °C. Bath/Bed | HC/$NH_3$/Air Ratio | Contact Time (Sec) | % Molar Yield MI | FN | MN | AN | MAH | % Conversion |
|---|---|---|---|---|---|---|---|---|---|---|
| 10 | $SbMo_2O_x + Mo°_{0.06}$ | 399/438 | 1/1.25/43.8 | 1.79 | 13.6 | 6.5 | 1.8 | 5.3 | 31.4 | 100.0 |
| 11 | $SbMo_2O_x + Mo°_{0.06}$ | 389/415 | 1/1.25/43.8 | 1.85 | 12.8 | 4.2 | 4.0 | 5.3 | 15.1 | 93.6 |
| 12 | $SbMo_{2.5}O_x + Mo°_{0.06}$ | 390/416 | 1/1.25/43.8 | 1.89 | 14.9 | 9.7 | 3.4 | 4.6 | 20.4 | 100.0 |
| 13 | $SbMo_{2.5}O_x + Mo°_{0.06}$ | 400/436 | 1/1.25/43.8 | 1.80 | 11.5 | 13.7 | 4.3 | 7.0 | 12.0 | 100.0 |
| 14 | $SbMo_3O_x + Mo°_{0.06}$ | 388/415 | 1/1.25/43.8 | 1.90 | 14.5 | 10.2 | 3.2 | 5.1 | 19.2 | 100.0 |
| 15 | $SbMo_3O_x + Mo°_{0.06}$ | 388/418 | 1/1.50/43.8 | 1.90 | 17.7 | 11.6 | 4.3 | 6.0 | 12.6 | 98.3 |
| 16 | $SbMo_{3.5}O_x + Mo°_{0.06}$ | 390/418 | 1/1.25/43.8 | 1.86 | 12.8 | 9.4 | 4.2 | 4.5 | 13.7 | 100.0 |
| 17 | $SbMo_{3.5}O_x + Mo°_{0.06}$ | 400/431 | 1/1.25/43.8 | 1.83 | 11.1 | 7.6 | 2.8 | 4.0 | 26.0 | 100.0 |
| 18 | $SbMo_4O_x + Mo°_{0.06}$ | 389/419 | 1/1.25/43.8 | 1.91 | 14.2 | 8.1 | 2.9 | 4.6 | 16.0 | 91.5 |
| 19 | $SbMo_4O_x + Mo°_{0.06}$ | 400/429 | 1/1.25/43.8 | 1.89 | 17.5 | 9.8 | 3.3 | 4.6 | 21.2 | 100.0 |

TABLE III

NITROGENATION OF 1,3 BUTADIENE - $SbMo_3Ti_{0.6}Nb_{0.1}O_xMo°_{0.06}$ CATALYST

| Example No. | Temp. °C. Bath/Bed | HC/$NH_3$/AIR Ratio | Contact Time (Sec.) | % Molar Yield MI | FN | MN | AN | MAH |
|---|---|---|---|---|---|---|---|---|
| 20 | 408/435 | 1/2.7/57 | 1.5 | 7.9 | 16.0 | 9.1 | 7.4 | 18.1 |
| 21 | 407/440 | 1/1.8/51 | 1.6 | 17.6 | 11.0 | 6.1 | 4.6 | 20.7 |
| 22 | 409/442 | 1/2.7/35.5 | 2.0 | 8.9 | 12.6 | 3.3 | 6.6 | 7.9 |
| 23 | 409/454 | 1/2.4/32.2 | 2.2 | 29.0 | 16.4 | 1.9 | 8.0 | 10.3 |
| 24 | 410/439 | 1/2.5/33.8 | 2.3 | 15.1 | 15.4 | 3.9 | 7.8 | 12.1 |
| 25 | 409/440 | 1/1.9/37.1 | 2.3 | 18.8 | 13.3 | 3.6 | 7.5 | 12.3 |
| 26 | 409/434 | 1/1.7/38 | 2.4 | 18.7 | 11.9 | 2.8 | 6.4 | 20.7 |
| 27 | 393/411 | 1/1/48.2 | 1.8 | 18.1 | 6.8 | 2.3 | 5.4 | 30.5 |
| 28 | 394/433 | 1/1.3/15.5 | 4.0 | 17.3 | 6.3 | 0 | 6.1 | 4.43 |
| 29 | 394/417 | 1/1.7/48.3 | 1.9 | 27.2 | 12.2 | 1.3 | 8.5 | 5.5 |
| 30 | 395/430 | 1/1.9/33.8 | 2.8 | 13.2 | 15.5 | 1 | 7.4 | 5.6 |

TABLE III-continued

NITROGENATION OF 1,3 BUTADIENE - SbMo$_3$Ti$_{0.6}$Nb$_{0.1}$O$_x$Mo°$_{0.06}$ CATALYST

| Example No. | Temp. °C. Bath/Bed | HC/NH$_3$/AIR Ratio | Contact Time (Sec.) | % Molar Yield | | | | |
|---|---|---|---|---|---|---|---|---|
| | | | | MI | FN | MN | AN | MAH |
| 31 | 393/414 | 1/2.1/63.5 | 1.8 | 16.8 | 15.4 | 2 | 8.6 | 11.0 |

TABLE IV

Nitrogenation of 1,3 Butadiene - Effect of Varying NH$_3$/Hydrocarbon Ratio*

| Example No. | Temp. °C. Bath/Bed | NH$_3$/HC Ratio | Contact Time (Sec.) | % Molar Yield | | | | | % Conversion |
|---|---|---|---|---|---|---|---|---|---|
| | | | | MI | FN | MN | AN | MAH | |
| SbMo$_3$O$_x$ + Mo°$_{0.06}$ | | | | | | | | | |
| 32 | 392/405 | 0 | 2.2 | 0 | 0 | 0 | 0 | 62.8 | 100 |
| 33 | 390/403 | 0.5 | 2.2 | 8.5 | 5.1 | 1.3 | 2 | 35.5 | 100 |
| 34 | 390/405 | 1.0 | 2.2 | 16.4 | 10.5 | 3.0 | 4.8 | 24.7 | 100 |
| 35 | 390/405 | 1.25 | 2.1 | 16.0 | 11.3 | 3.7 | 6.1 | 15.3 | 100 |
| 36 | 390/409 | 1.5 | 2.1 | 15.0 | 12.8 | 4.6 | 5.1 | 7.0 | 100 |
| 37 | 390/411 | 2.0 | 2.1 | 5.3 | 14.4 | 4.4 | 6.1 | 28.3 | 100 |
| SbMo$_3$Ti$_{0.6}$Nb$_{0.1}$ + Mo°$_{0.06}$ | | | | | | | | | |
| 38 | 394/410 | 0.5 | 1.9 | 8.0 | 4.5 | 1.2 | 2.4 | 44.9 | 83.1 |
| 39 | 395/413 | 1.18 | 1.9 | 20.9 | 10.7 | 2.3 | 5.9 | 17.4 | 100 |
| 40 | 395/415 | 1.25 | 1.9 | 17.7 | 10.2 | 2.3 | 5.8 | 17.5 | 100 |
| 41 | 395/417 | 2.0 | 1.9 | 17.3 | 14.8 | 3.6 | 6.9 | 16.2 | 100 |
| 42 | 394/417 | 2.5 | 1.8 | 4.8 | 14.5 | 4.1 | 6.4 | 9.1 | 100 |

*AIR/HC Ratio = 44

TABLE V

Nitrogenation of 1,3 Butadiene - Effect of Various Contact Time - SbMo$_3$O$_x$ + Mo°$_{0.06}$ Catalyst*

| Example No. | Temp. °C. Bath/Bed | Contact Time (Sec.) | % Yield | | | | | % Conversion |
|---|---|---|---|---|---|---|---|---|
| | | | MI | FN | MN | AN | MAH | |
| 43 | 395/405 | 4.3 | 22.0 | 12.1 | 1 | 7.2 | 11.8 | 100 |
| 44 | 395/407 | 3.2 | 20.8 | 12.3 | 1.0 | 7.3 | 10.0 | 100 |
| 45 | 395/409 | 2.2 | 17.6 | 12.0 | 3.3 | 6.0 | 13.3 | 100 |
| 46 | 395/409 | 1.0 | 11.3 | 12.1 | 6.4 | 4.6 | 11.7 | 90.3 |

*HC/NH$_3$/AIR Ratio = 1/1.25/43.8

TABLE VI

Maleimide Production Mechanism Study Using - SbMo$_3$O$_x$ + Mo°$_{0.06}$ Catalyst

| Example No.* | Temp. °C. Bath/Bed | HC/NH$_3$/AIR Ratio | Contact Time Sec. | % Yield | | | | |
|---|---|---|---|---|---|---|---|---|
| | | | | MI | FN | MN | AN | MAH |
| C 47 | 390/405 | 1/1.5/43.8 | 2 | — | 1 | 5.6 | 7.4 | 15.5 |
| C 48 | 390/414 | 1/0/43.8 | 1 | — | — | — | — | 58.7 |
| C 49 | 390/414 | 1/1.5/43.8 | 1 | — | — | — | — | 43.5 |
| C 50 | 390/406 | 1/1.5/43.8 | 1 | — | 0.2 | — | 0.8 | — |
| C 51 | 392/416 | 1/1.5/43.8 | 1 | — | 1.2 | 0.5 | 0.8 | — |
| 52 | 390/422 | 1/1.5/43.8 | 2 | 12.9 | 9.6 | 3.1 | 5.9 | 13.9 |

C — Comparative Examples

The above Examples of the invention are provided to demonstrate operability and are not intended to limit the scope of the invention. For example, N-substituted cyclic imides can be prepared according to the process of the present invention, using as a hydrocarbon feedstock, for instance, the butenes or butadiene. Illustrations of such embodiments include but are not limited to the following. N-substituted cyclic imides are produced by contacting butadiene, oxygen and a primary amine in the vapor phase, at temperatures from about 375° C. to about 475° C., preferably 390° C. to about 430° C. in the presence of an oxidation catalyst, preferably containing molybdenum oxide.

TABLE VII

| Primary Amine | N—Substituted Maleimide Product |
|---|---|
| Methylamine | N—Methylmaleimide |
| Ethylamine | N—Ethylmaleimide |
| Propylamine | N—Propylmaleimide |
| n-Butylamine | N—n-Butylmaleimide |
| Cyclohexylamine | N—Cyclohexylmaleimide |
| Phenylamine | N—Phenylmaleimide |
| p-Tolylamine | N—p-Tolylmaleimide |
| Xylylamine | N—Xylylmaleimide |
| 3,4-Dichlorophenylamine | N—3,4-Dichlorophenylmaleimide |
| Allylamine | N—Allylmaleimide |
| Isoamylamine | N—Isoamylmaleimide |

The primary amines listed above are known and may be prepared by methods apparent to those in the art.

Other oxidation catalysts suitable for the nitrogenation process of the present invention include, but are not limited to, the following.

TABLE VIII

| | |
|---|---|
| VFeSb$_3$Mo$_{12}$O$_x$ | Mo$_{12}$P$_{1.32}$Bi$_{0.5}$Cu$_{0.25}$Cl$_{0.06}$O$_x$ |
| BFeVSb$_3$Mo$_{12}$O$_x$ | Ni$_{0.2}$Cu$_{0.25}$Mo$_{12}$P$_{1.32}$Rb$_2$O$_x$ |
| Mg$_{0.12}$Sb$_4$Mo$_6$O$_x$ | Mg$_{0.12}$P$_{1.32}$As$_{0.5}$Cu$_{0.2}$Cr$_4$O$_x$ |
| Li$_{0.1}$SbMo$_3$V$_{0.1}$ + W°$_{0.06}$ | Mo$_3$P$_{0.33}$Ti$_{0.5}$O$_x$ |
| SbMo$_3$Fe$_{0.2}$V$_{0.1}$ + W°$_{0.06}$ | Mo$_{12}$V$_3$Ge$_{1.0}$Cu$_{0.5}$O$_x$ |
| Ce$_{0.1}$SbMo$_3$V$_{0.1}$O$_x$ + W°$_{0.06}$ | Mo$_{12}$V$_3$W$_{1.2}$Re$_{0.2}$O$_x$ |
| VMo$_{0.2}$P$_{1.2}$O$_x$ | Sn$_6$W$_{1.2}$V$_3$Mo$_{12}$O$_x$ |
| Mg$_{4.5}$Ni$_{2.5}$Fe$_3$BiP$_{0.5}$Mo$_{12}$O$_x$ | Sb$_3$Fe$_6$Pd$_{0.25}$O$_x$ |

Thus it should be apparent to those skilled in the art that the subject invention accomplishes the objects set forth above. It is to be understood that the subject invention is not to be limited by the examples set forth herein. These have been provided merely to demonstrate operability, and the selection of oxidation catalysts, nitrogenating agents, hydrocarbon feedstocks and reaction conditions can be determined from the total specification disclosure provided without departing from the spirit of the invention herein disclosed and described, the scope of the invention including equivalent embodiments, modifications and variations that fall within the scope of the attached claims.

We claim:

1. A process for the direct synthesis of maleimide which does not proceed through maleic anhydride as a intermediate, the process comprising contacting in the vapor phase an unsaturated hydrocarbon having from 4 to about 9 carbon atoms with ammonia and molecular oxygen or a molecular oxygen-containing gas in the presence of an oxidation catalyst having variable valency metal oxides; and recovering said maleimide.

2. The process in accordance with claim 1 wherein said unsaturated hydrocarbon is butadiene.

3. The process in accordance with claim 1 wherein the ratio of ammonia to hydrocarbon ranges from about 0.5:1 to about 2:1.

4. The process in accordance with claim 1 wherein the ratio of ammonia to hydrocarbon ranges from about 0.75:1 to about 1.75:1.

5. The process in accordance with claim 1 wherein the ratio of oxygen to hydrocarbon ranges from about 2:1 to about 30:1.

6. The process in accordance with claim 1 wherein said catalyst comprises the oxide of at least one of molybdenum and antimony.

7. The process in accordance with claim 4 wherein said catalyst contains the oxide of a promoter element selected from at least one of titanium, zirconium, niobium, tantalum, vanadium, iron, aluminum, zinc, cadmium, platinum, ruthenium, boron, germanium, tin, phosphorus, arsenic, bismuth, tellurium, silver, the rare earths, thallium thorium, uranium, the alkali metals, and the alkaline earth metals.

8. The process in accordance with claim 1 wherein said catalyst is molybdenum oxide.

9. The process in accordance with claim 1 wherein said catalyst is molybdenum oxide and antimony oxide.

10. The process in accordance with claim 1 wherein said catalyst is molybdenum oxide and antimony oxide promoted with titanium oxide and niobium oxide.

11. The process in accordance with claim 1 wherein said process occurs at a temperature between about 25° C. and about 600° C.

12. The process in accordance with claim 1 wherein said process occurs at a temperature between about 375° C. and about 475° C.

13. The process in accordance with claim 1 wherein said maleimide is recovered by passing a stream containing said sythesized maleimide through a scrubber solution containing an acidified solvent.

14. The process in accordance with claim 13 wherein said solvent is an aqueous solution of a mineral acid, said solution having a pH of less than 7.

* * * * *